United States Patent [19]

Takarada et al.

[11] Patent Number: 5,737,078
[45] Date of Patent: Apr. 7, 1998

[54] CYTOANALYZER USING SEPARATE SENSING PORTIONS ON A DECTECTOR AND METHOD FOR ALIGNING THE SAME

[75] Inventors: Kaoru Takarada, Miki; Takashi Sakata, Kakogawa; Yoshihiro Hyosa, Kobe; Chihiro Kouzuki, Kasai, all of Japan

[73] Assignee: TOA Medical Electronics Co., Ltd., Hyogo, Japan

[21] Appl. No.: 512,647

[22] Filed: Aug. 8, 1995

[30] Foreign Application Priority Data

Aug. 8, 1994 [JP] Japan .................................. 6-186148

[51] Int. Cl.[6] .......................... G01N 21/00; G01J 1/42
[52] U.S. Cl. .......................... 356/338; 356/340; 356/343; 356/336; 250/208.6; 250/574
[58] Field of Search ................. 356/73, 338, 340–341, 356/343, 399; 250/208.6, 574

[56] References Cited

U.S. PATENT DOCUMENTS

| 3,830,569 | 8/1974 | Meric . | |
|---|---|---|---|
| 4,595,291 | 6/1986 | Tatsuno | 356/343 |
| 4,596,035 | 6/1986 | Gershman et al. . | |
| 5,105,093 | 4/1992 | Niwa | 356/336 |
| 5,125,737 | 6/1992 | Rodriguez et al. | 356/338 |
| 5,416,580 | 5/1995 | Trainer | 356/343 |
| 5,467,193 | 11/1995 | Laewen et al. | 356/399 |
| 5,538,893 | 7/1996 | Sakata et al. | 436/10 |

FOREIGN PATENT DOCUMENTS

| 60-260830 | 12/1985 | Japan . |
| 1-502533 | 8/1989 | Japan . |
| 3-233344 | 10/1991 | Japan . |
| WO8504014 | 9/1985 | WIPO . |

OTHER PUBLICATIONS

Patent Abstracts of Japan–60–260830 dated Dec. 24, 1985.
"Improved Multilaser/Multiparameter Flow Cytometer for Analysis and Sorting of Cells and Particles", Steinkamp J. A., et al., Review of Scientific Instruments, vol. 62, No. 1, Nov. 1, 1991, pp. 2751–2764.

Primary Examiner—Frank G. Font
Assistant Examiner—Jason D. Vierra-Eisenberg

[57] ABSTRACT

A cytoanalyzer includes a flow cell for aligning cells and permitting the same to pass therethrough, a semiconductor light emitting device for emitting a laser beam to the cells passing through the flow cell, and a light-detecting device having at least two separate photosensing portions capable of sensing two types of light scattered by each of the cells. The alignment of the cytoanalyzer may be achieved by comparing intensities of light on the at least two separate photosensing portions.

19 Claims, 11 Drawing Sheets

DETECTOR AREA OF PD

PHOTODIODE (PD)

DECYLTRIMETHYLAMMONIUM BROMIDE 750 mg/l

OPTICAL AXIS IS CORRECTLY ADJUSTED.
A - E = 0
B - D = 0
C IS MAXIMUM(=Cm)

FIG. 8(c)

OPTICAL AXIS IS UPWARDLY OFFSET.
A - E > 0
B - D = 0
C < Cm

FIG. 8(d)

OPTICAL AXIS IS DOWNWARDLY OFFSET.
A - E < 0
B - D = 0
C < Cm

FIG. 8(e)

OPTICAL AXIS IS OFFSET TO LEFT.
A - E = 0
B - D > 0
C < Cm

FIG. 8(f)

OPTICAL AXIS IS OFFSET TO RIGHT.
A - E = 0
B - D < 0
C < Cm

*FIG. 9(a)*  BEAM STOPPER IS LOCATED IN CENTER.
A - E = 0
B - D = 0
C SHOWS MINIMUM VALUE(=Cmin).

*FIG. 9(b)*  BEAM STOPPER IS OFFSET TO LEFT.
A - E = 0
B - D < 0
C > Cmin

*FIG. 9(c)*  BEAM STOPPER IS OFFSET TO RIGHT.
A - E = 0
B - D > 0
C > Cmin

CYTOANALYZER USING SEPARATE SENSING PORTIONS ON A DECTECTOR AND METHOD FOR ALIGNING THE SAME

BACKGROUND OF THE INVENTION

1. Field of the Invention

The present invention relates to cytoanalyzers for classifying and counting cells and, more particularly, to cytoanalyzers for analyzing cells by emitting a light beam to cells in a fine stream and sensing light scattered thereby.

2. Description of Related Art

In the field of clinical analysis, it is essential to classify and quantify leukocytes, reticulocytes and the like in a whole blood sample of a patient for diagnosis of various diseases. To this end, various analyzers have been proposed. One exemplary analyzer measures such parameters as RF signal intensity (signal generated on the basis of variation in electrical impedance in radio frequency), DC signal intensity (signal generated on the basis of variation in electrical impedance (electrical resistance) in direct current), fluorescent intensity, scatter light intensity, absorbance and depolarized scatter light intensity to classify leukocytes into subclasses (lymphocyte, monocyte, neutrophil, eosinophit and basophit).

In the analyzer, a blood sample sucked by a sample sucking section is automatically pretreated and then introduced to a detecting section. The number or content of cells of a specific subclass is determined by counting and analyzing signals detected by the detecting section and is output.

In the flow cytometer, a sample solution is prepared by diluting a blood sample and staining blood cells included therein; and then a fine stream of the sample solution is passed through a central potion of a flow cell. In a sensing section thereof, a beam emitted from a light source is finely focused onto the fine stream of the sample solution, and light scattered by each blood cell passing through the sensing section and fluorescent variation are detected by photosensors. The classification and quantification of particular blood cells are achieved by preparing a two-dimensional distribution diagram based on detected signals, for example, with the scatter light intensity and fluorescent intensity being plotted on two axes.

Figure 10:
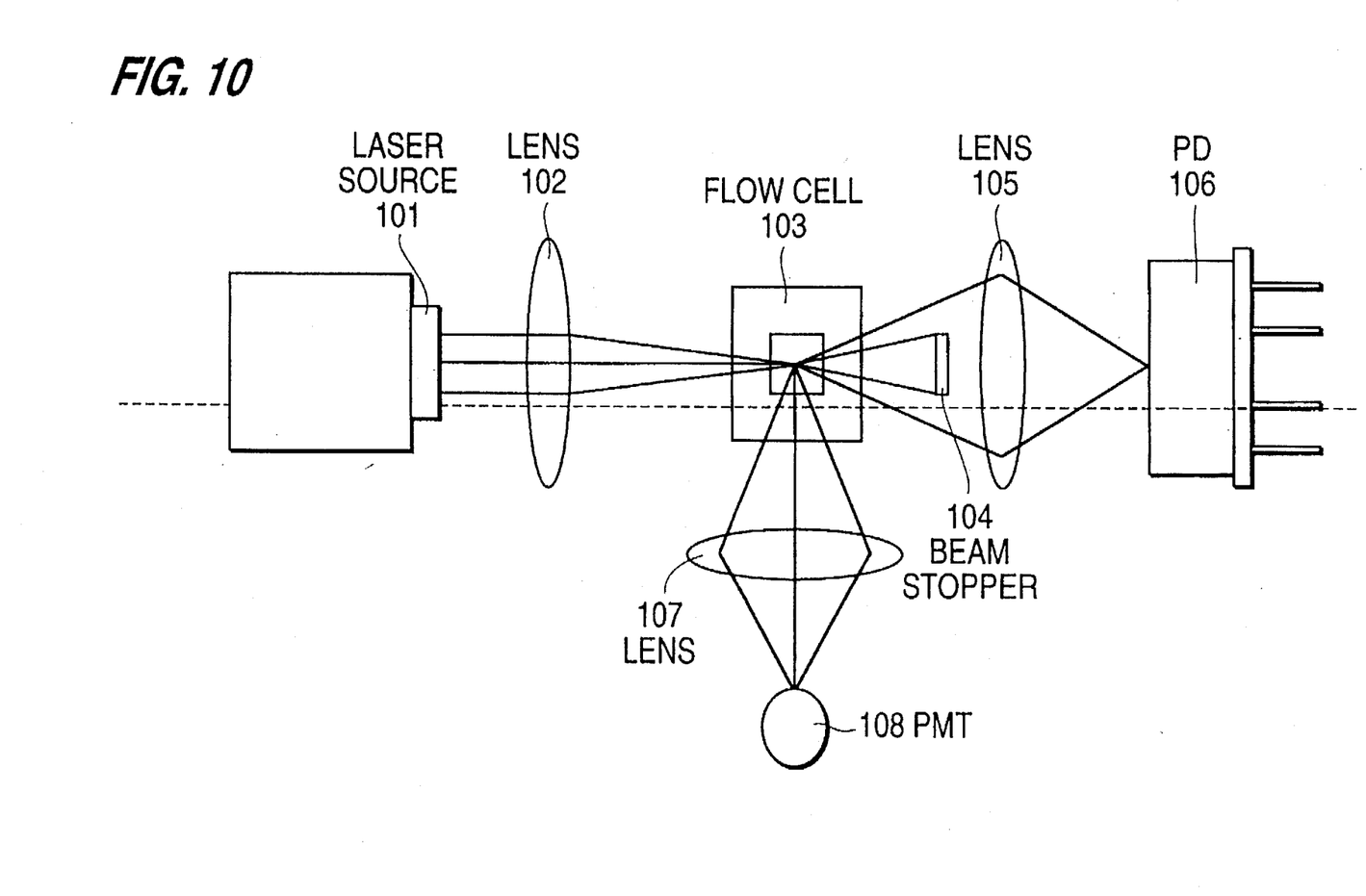
FIG. 10 is a diagram illustrating a construction of one exemplary conventional cytoanalyzer.

FIG. 10 illustrates one example of a conventionally available cytoanalyzer. A light source 101 employs an argon ion laser or He-Ne laser. Light emitted from the light source 101 is condensed by a lens 102 and directed to cells in a fine stream passing through a central portion of a flow cell 103.

Light meeting the cells is scattered, and side scatter light is concentrated by a lens 107 onto a photomultiplier tube (PMT) 108. Forward scatter light (in the same direction as the traveling direction of the emitted light) is concentrated by a lens 105 onto a photodiode (PD) 106. In FIG. 10, a reference numeral 104 denotes a beam stopper for preventing the incidence of direct light emitted from the light source onto the PD 106. The "direct light" means light passing through the flow cell without being scattered by the cells.

The classification of blood cells can be realized by sensing side scatter light and forward scatter light and measuring the intensity of light signals thereof. For example, more than three subclasses of unstained leukocytes can be discriminated from each other on the basis of signals indicative of the intensities of side scatter light and forward scatter light by means of the analyzer shown in FIG. 10.

Figure 11:
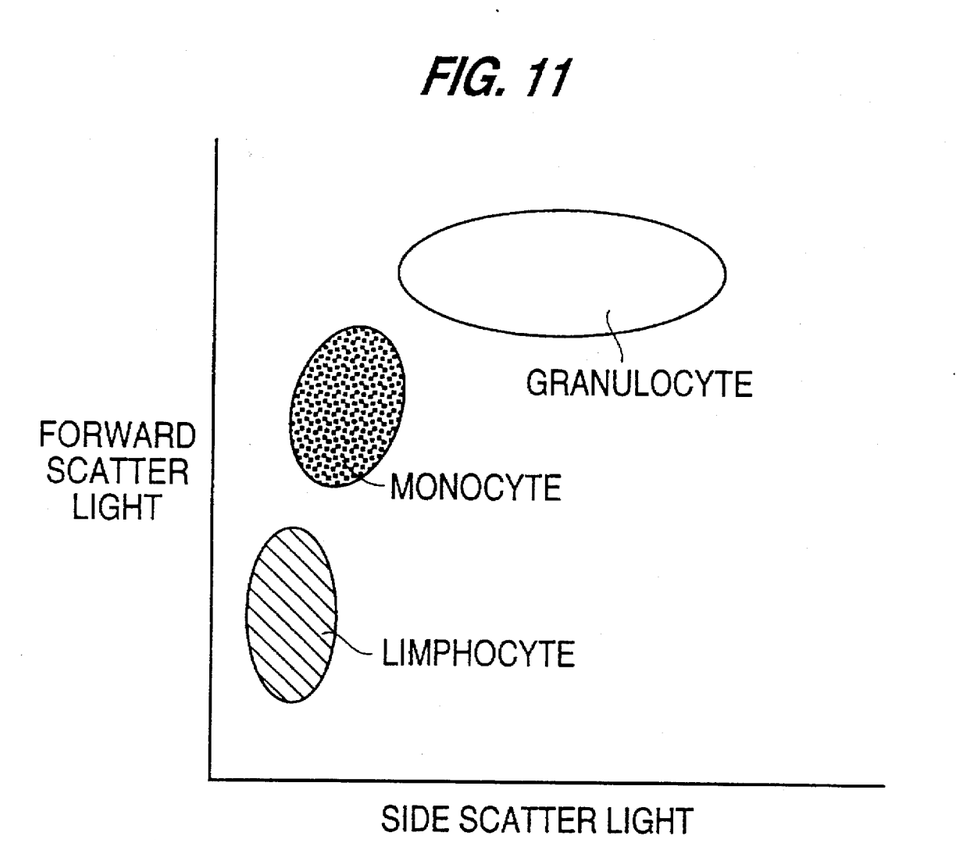
FIG. 11 is a scattergram for classification of leukocytes obtained by a conventional cytoanalyzer.

FIG. 11 illustrates one exemplary scattergram in which the light intensity signals of side scatter light and forward scatter light are plotted on two axes. In FIG. 11, the intensities of the side scatter light and the forward scatter light are plotted as the abscissa and the ordinate, respectively. As shown, leukocytes are classified into three subclasses, i.e., lymphocyte, monocyte and granutocyte.

Figure 12:
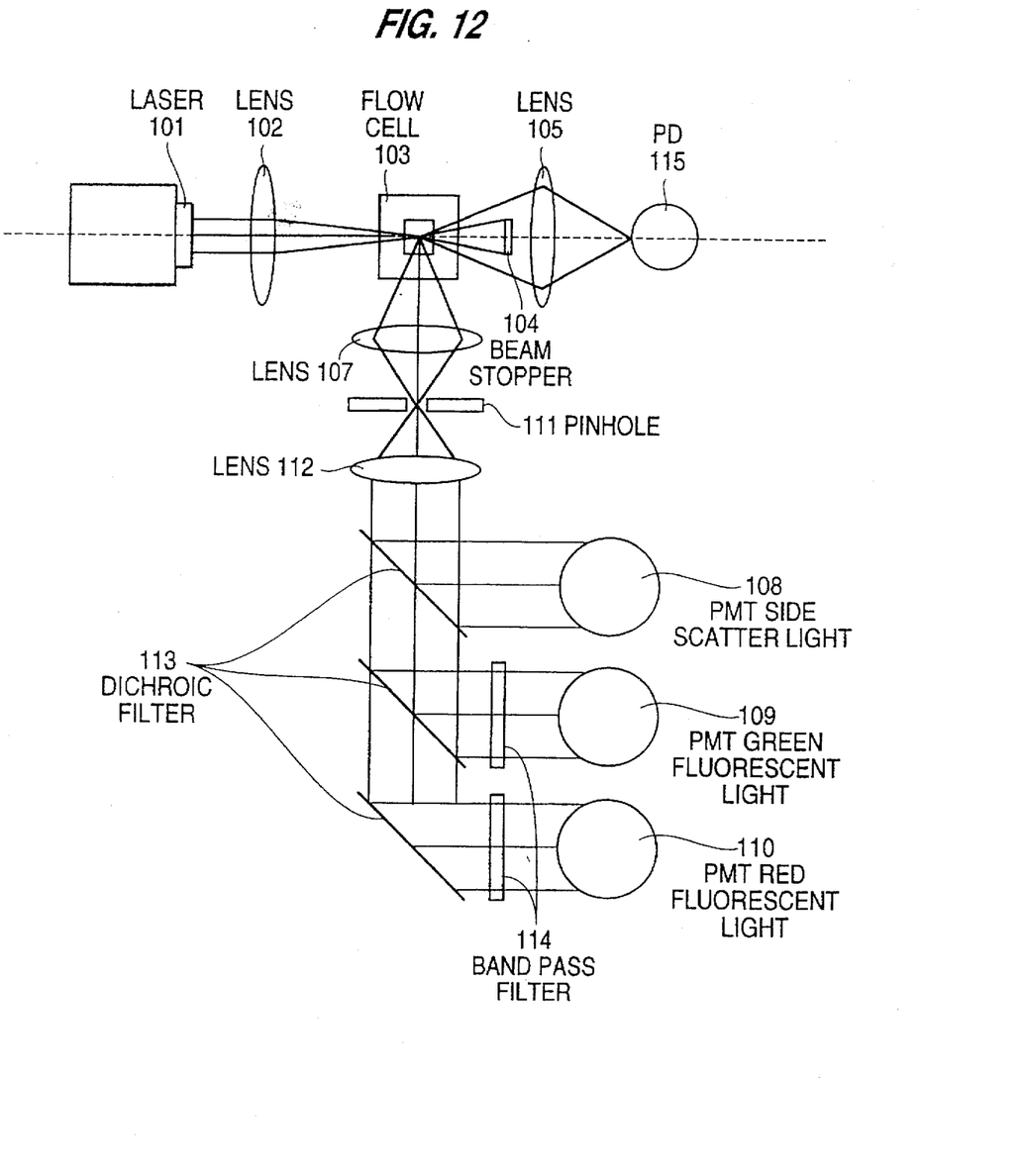
FIG. 12 is a diagram illustrating a construction of another exemplary conventional cytoanalyzer.

FIG. 12 illustrates another exemplary cytoanalyzer. This cytoanalyzer is adapted to analyze blood cells by sensing forward scatter light, side scatter light and fluorescent light, for example, to identify at least four leukocyte subclasses.

As shown in FIG. 12, the cytoanalyzer includes, in addition to the components shown in FIG. 10, a pin hole 111, a dichroic filter 113 for selectively filtering light of a particular wavelength, a band pass filter 114, photomultiplier tubes (PMT) 109 and 110 for detecting fluorescent light, and a photodiode (PD) 115. The cytoanalyzer further requires fluorescent dye for fluorescently stain leukocytes for the detection of fluorescent light.

Japanese Unexamined Patent Publication No. SHO 60-260830 discloses a light source system for light emission onto cells in an automatic cytoanalyzer in which two light sources, i.e., a laser diode (semiconductor laser) and a flash lamp, are employed.

With the light source system, the passage of each cell is detected by applying a laser beam emitted from the laser diode onto each cell and measuring light scattered forward thereby. In synchronization with the detection, the flash lamp is activated to emit light to the cell for the detection of fluorescent light emitted therefrom.

Japanese Unexamined Patent Publication No. HEI 3-233344 discloses an optical particle analyzer having two kinds of light sources, i.e., a laser diode and a tamp such as a halogen lamp. The optical particle analyzer is adapted to detect scattered light and fluorescent light for classification and quantification of particles.

Japanese Unexamined Patent Publication (PCT) No. HEI 1-502533 discloses a cytoanalyzer for identifying leukocyte subclasses by measuring scatter light intensity, RF signal and DC signal. The cytoanalyzer is adapted to measure low-angle scatter light which is scattered at angles between 0.5° and 2.0° with respect to an optical axis and medium-angle scatter light which is scattered at angles between 10° and 70° with respect to the optical axis. After passing through beam stoppers for blocking light traveling at angles other than desired angles, the low-angle scatter light and medium-angle scatter light are detected as electrical signals by means of a photodiode (PD).

In such cytoanalyzers, a light beam must be focused on a fine stream flowing through a flow cell thereof, and further an optical axis is required to be adjusted so as to focus the scattered light on a photomultiplier tube by moving optical system components such as lens and beam stopper. In the conventional practice, an operator carries out manual adjustment of these optical system components through visual observation of a light beam while allowing a standard sample to flow through a flow cell, before the analysis of a blood sample.

However, in many cases, a cytoanalyzer of the type shown in FIG. 10 or 12 employs an expensive argon ion laser or He-Cd laser for a light source system, since the cytoanalyzer detects side scatter light which is weak than forward scatter light and is required to utilize blue light of a relatively short wavelength as excitation light to cause cells to emit fluorescent light.

Such a light source system is not only expensive but also occupies a large space in the cytoanalyzer because a large laser generator and other peripherals such as power supply for driving the laser are incorporated therein. In addition, the cytoanalyzer consumes a large power and requires a high maintenance cost.

Further, the cytoanalyzer requires the condenser lens 107 for collecting the side scatter light and the expensive photomultiplier tube (PMT). The cytoanalyzer shown in FIG. 12, in particular, requires many filters for selectively detecting fluorescent light, and is thereby rendered complicated and large-scale.

The light source system disclosed in Japanese Unexamined Patent Publication No. SHO 60-260830, which employs two types of light sources for the detection of scattered light and fluorescent light, is required to adjust the timing of light emission of the flash tamp, and is thereby rendered complicated and expensive.

The cytoanalyzer disclosed in Japanese Unexamined Patent Publication (PCT) No. HEI 1-502533 requires a plurality of beam stoppers for blocking unnecessary scattered light to obtain only two types of light rays scattered at angles in predetermined ranges. This requires difficult positional adjustment of scatter light detectors and beam stoppers.

The optical particle analyzer disclosed in Japanese Unexamined Patent Publication No. HEI 3-233344 which employs two types of light sources requires a complicated and expensive optical system for light emission.

The adjustment of the optical system conventionally implemented through visual observation needs a complicated operation requiring a skill, and is influenced by the difference in the skill among individual operators. Therefore, it is difficult to accurately adjust the positions of the optical system components to ensure the best performance of the system.

SUMMARY OF THE INVENTION

It is an object of the present invention to provide a compact and inexpensive cytoanalyzer for analyzing cells by applying a laser beam emitted from a compact light emitting means onto cells in a fine stream and detecting two types of light by light-detecting means having at least two separate photosensing portions.

It is another object of the present invention to provide a compact and inexpensive cytoanalyzer which employs a laser diode as a light source and a photodiode as a light-detecting device.

It is still another object of the present invention to classify and count leukocytes by employing the aforesaid cytoanalyzer to detect and analyze the two types of light.

It is yet another object of the present invention to provide a cytoanalyzer including a light-detecting device having a plurality of separate light-detecting surfaces for detecting two types of light to permit easy adjustment of the optical system thereof.

In accordance with one aspect of the present invention, there is provided a cytoanalyzer comprising: a flow cell for aligning cells and permitting the same to pass therethrough; semiconductor light emitter for emitting a laser beam to the cells passing through the flow cell; and light-detector having at least two separate photosensing portions capable of sensing two types of light come from each of the cells.

The cytoanalyzer may further includes: first light condenser for focusing a laser beam emitted from the semiconductor light emitter on the flow cell; second light condenser for condensing the two types of light come from the cell so as to direct the same substantially parallel to an optical axis of the laser beam emitted from the semiconductor light emitter; and a beam stopper for blocking the passage of light directly emitted thereto from the semiconductor light emitter, wherein the light-detector detects the two types of forward scatter light directed substantially parallel to the optical axis by the second light condenser.

Thus, the present invention realizes a compact and inexpensive cytoanalyzer, which is adapted to utilize a Easer beam emitted from the semiconductor light emitter and detect the two types of light by the light-detector means having at least two photosensing portions.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
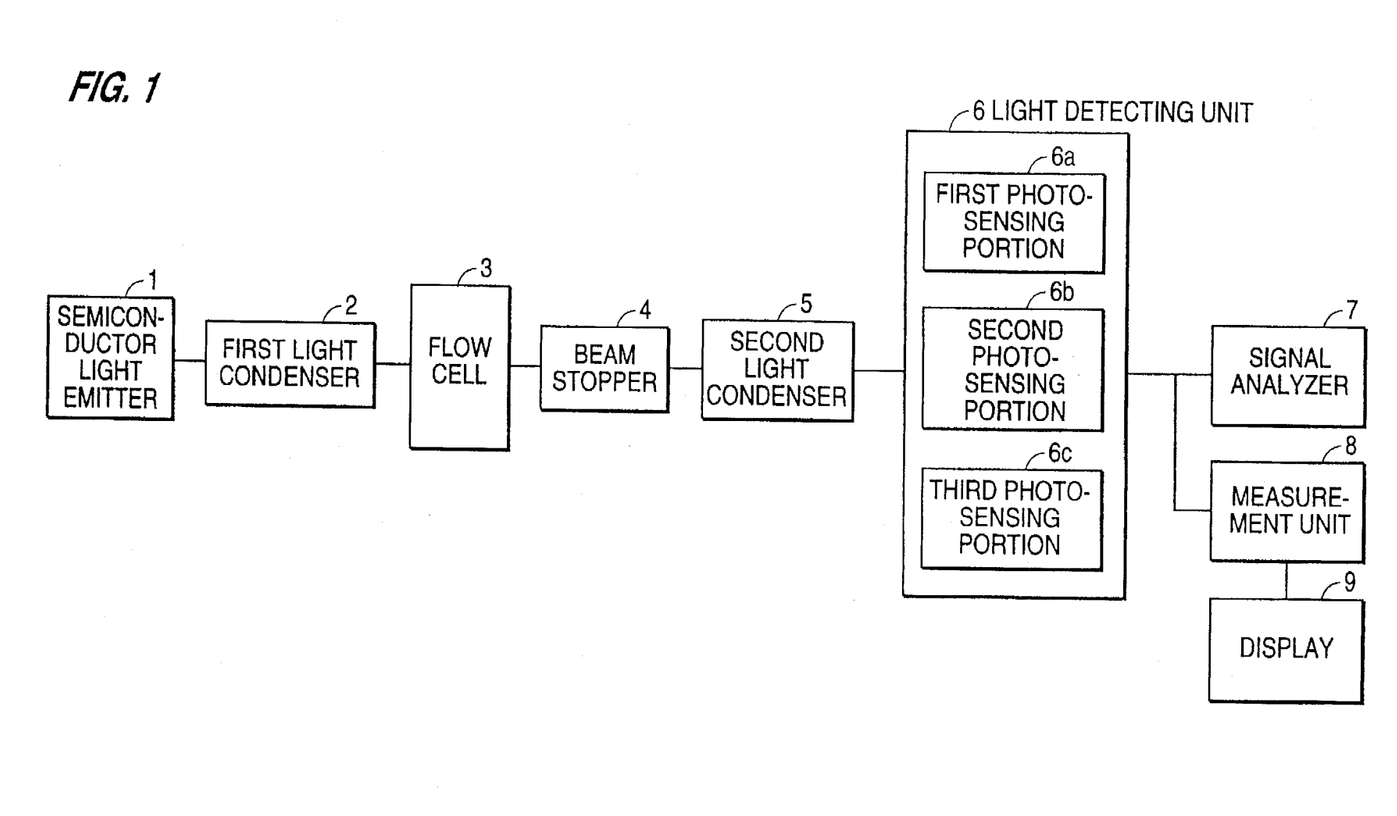
FIG. 1 is block diagram illustrating a basic construction of a cytoanalyzer in accordance with the present invention.

FIG. 1 is a block diagram illustrating the basic construction of a cytoanalyzer in accordance with the present invention. As shown, the cytoanalyzer comprises: a flow cell 3 adapted to align cells and permit them to pass therethrough; a semiconductor light emitter 1 for emitting a laser beam to the cells passing through the flow cell 3; and a light-detector 6 having at least two separate photosensing portions capable of sensing two types of light come from each of the cells.

The cytoanalyzer may further include: first a light condenser 2 for focusing a laser beam emitted from the semiconductor light emitter 1 on the flow cell 3; a second light condenser means 5 for condensing the two types of light come from the cell so as to direct the same substantially parallel to an optical axis of the laser beam emitted from the semiconductor light emitter 1; and a beam stopper 4 for blocking the passage of light directly emitted thereto from the semiconductor light emitter. The light-detector 6 is adapted to detect the two types of forward scatter light directed substantially parallel to the optical axis by the second light condenser 5.

The light-detector 6 preferably includes a first photosensing portion 6a for detecting light rays scattered forward at low angles with respect to the optical axis and a second photosensing portion 6b for detecting light rays scattered forward at high angles with respect to the optical axis. The light-detecting means 6 preferably comprises a photodiode.

The semiconductor light emitter 1 preferably comprises a semiconductor laser device (laser diode) capable of emitting a laser beam having a wavelength (e.g., 650 nm) in the visible spectrum. Exemplary semiconductor laser devices include LASER DIODE TOLD9421 available from Toshiba Corporation.

In the light-detector 6, the first photosensing portion 6a preferably has one light-detecting surface, and the second photosensing portion 6b preferably has two light-detecting surfaces disposed symmetrically with respect to a first axis, with the first photosensing portion 6a interposed therebetween. The light-detector 6 preferably further includes a third photosensing portion 6c having two light-detecting surfaces disposed symmetrically with respect to a second axis extending perpendicular to the first axis, with the first photosensing portion 6a interposed therebetween.

The cytoanalyzer may further include signal analyzer 7 for analyzing pulse signals indicative of the two types of forward scatter light detected by the light-detecting means 6, and may be adapted to detect the two types of light rays scattered forward by leukocytes in a fine stream passing through the flow cell 3 by the semiconductor light-detector 6 and classify the leukocytes by the signal analyzer 7.

The cytoanalyzer preferably further includes a measurement unit 8 for determining output differences among light intensities detected by the first, second and third photosensing portions 6a, 6b and 6c, and a display 9 for displaying measurement results obtained by the measurement unit 8.

The present invention will hereinafter be described in detail by way of embodiments thereof shown in the attached drawings. These embodiments are not intended to limit the present invention.

Figure 2:
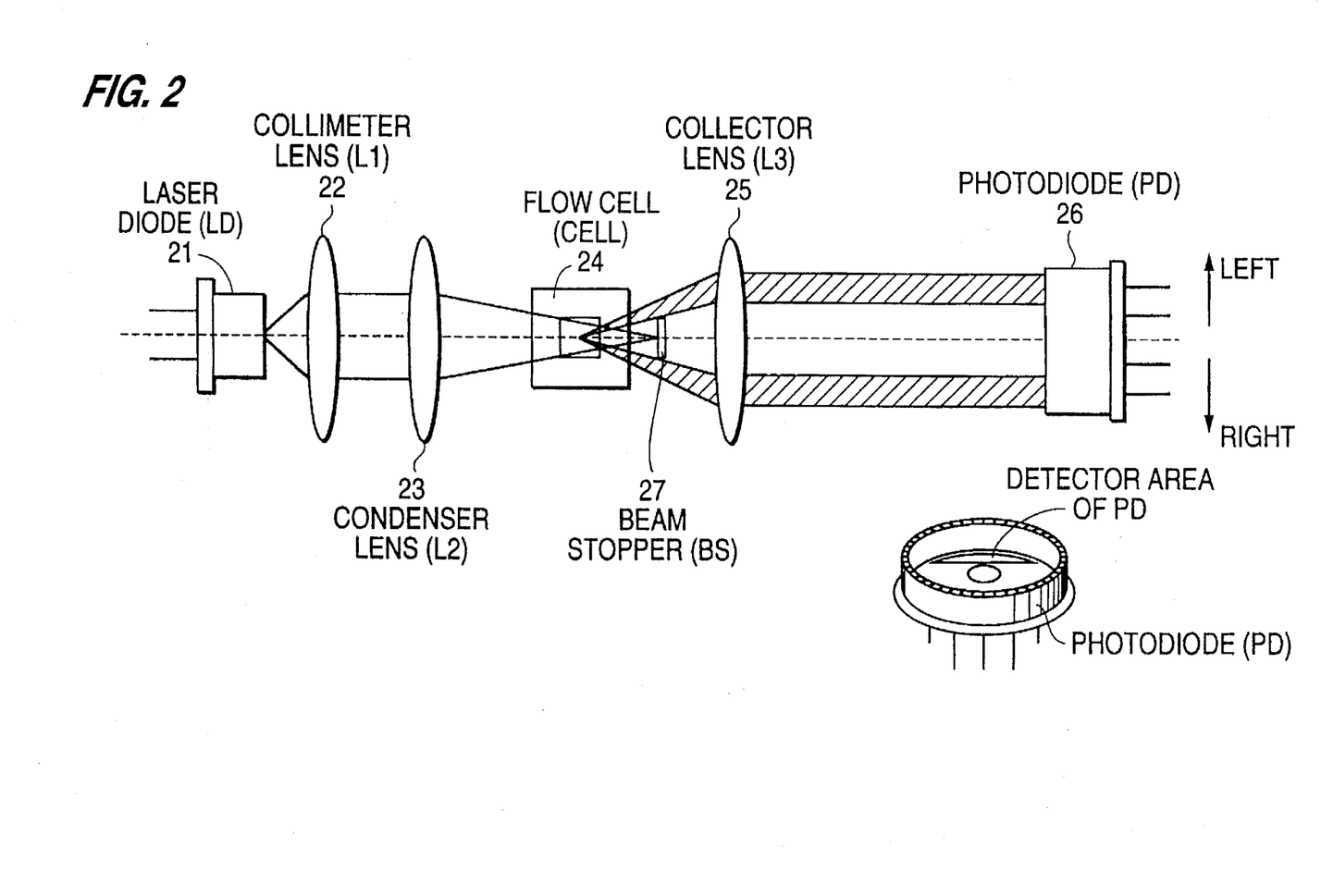
FIG. 2 is a plan view illustrating a construction of a cytoanalyzer in accordance with one embodiment of the present invention.
Figure 3:
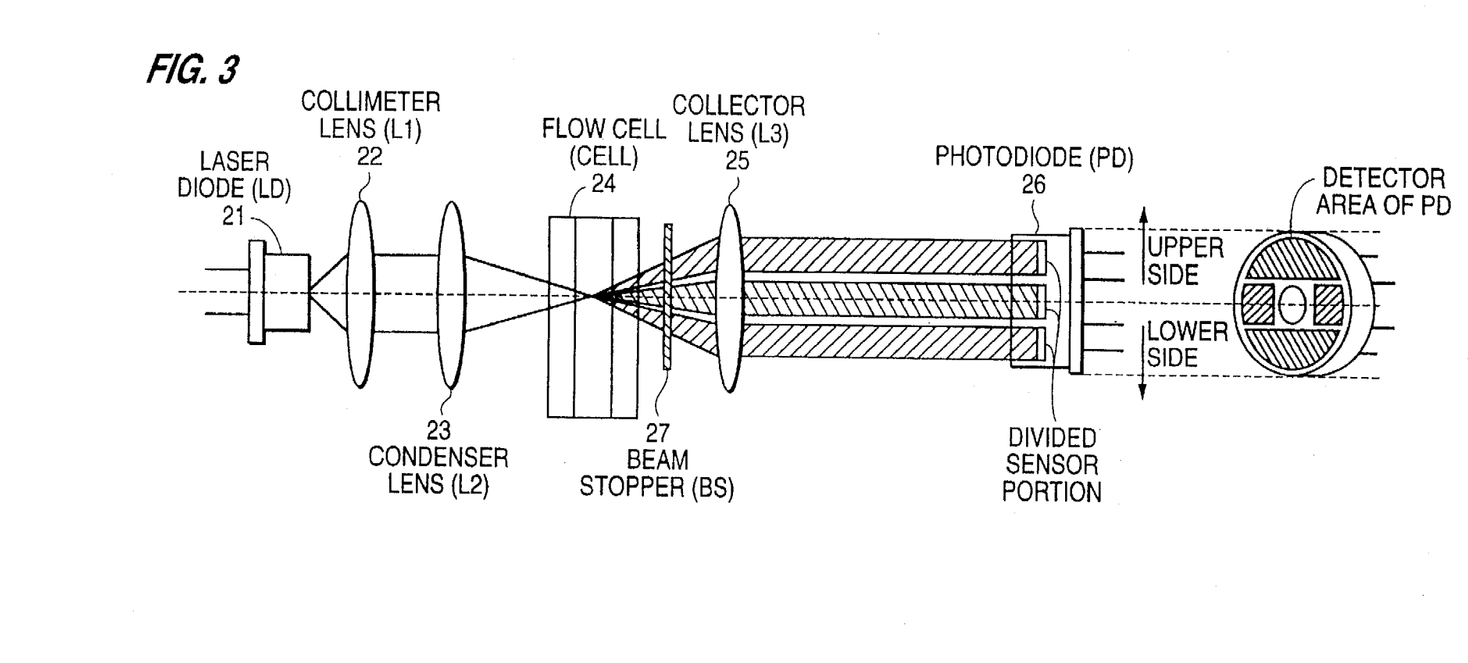
FIG. 3 is a side view illustrating the construction of the cytoanalyzer in accordance with one embodiment of the present invention.

FIGS. 2 and 3 illustrate the construction of a cytoanalyzer in accordance with one embodiment of the present invention as viewed from the top and the side, respectively. As shown, components of the cycoanalyzer are arranged in a line on an optical axis.

Referring to FIGS. 2 and 3, the cytoanalyzer includes a laser diode (LD) 21, a collimator lens (L1) 22, a condenser lens (L2) 23, a flow cell (CELL) 24, a beam stopper (BS) 27, a collector lens (L3) 25 and a photodiode (PD) 26.

The laser diode 21 comprises, for example, LASER DIODE TOLD9421 (maximum light output: 5 mW, output wavelength: 650 nm) available from Toshiba Corporation. In contrast with a typical argon ion laser having dimensions of about 15×15×40 (cm), this laser diode has a diameter of about 10 mm, thereby contributing to a reduction in the size of the cytoanalyzer.

The collimator lens 22 and condenser lens 23 cooperatively focus a laser beam emitted from the laser diode 21 onto a portion of the flow cell 24 through which cells pass. A fine stream of blood pretreated with a reagent is allowed to flow through the flow cell 24. The direction of the flow is from the back side to the front side of the drawing of FIG. 2, or from the upper side to the lower side of the drawing of FIG. 3.

On the downstream of the flow cell 24 in the optical system or on a side opposite to the laser diode 21 am disposed the beam stopper 27, the collector lens 25 arranged adjacent thereto, and the photodiode 26 serving as a light-detecting device arranged a little away therefrom. The beam stopper 27 is a vertically elongated plate for blocking the laser beam passing through the central portion of the flow cell 24. The collector lens 25 serves to condense light rays scattered forward by the cells passing through the flow cell 24 and direct the light rays parallel To the optical axis.

The photodiode 26 serves as a photoelectric convertor device for detecting the forward scatter light and converting the intensity of the light into an electrical pulse signal. The use of the photodiode 26 as the detector which is compact and inexpensive is the most preferable, but other detectors may be employed.

The photodiode 26 which is adapted to detect the forward scatter light directed parallel to the optical axis by the collector lens 25 has a plurality of separate light-detecting surfaces capable of detecting two types of forward scatter light rays.

Figure 4:
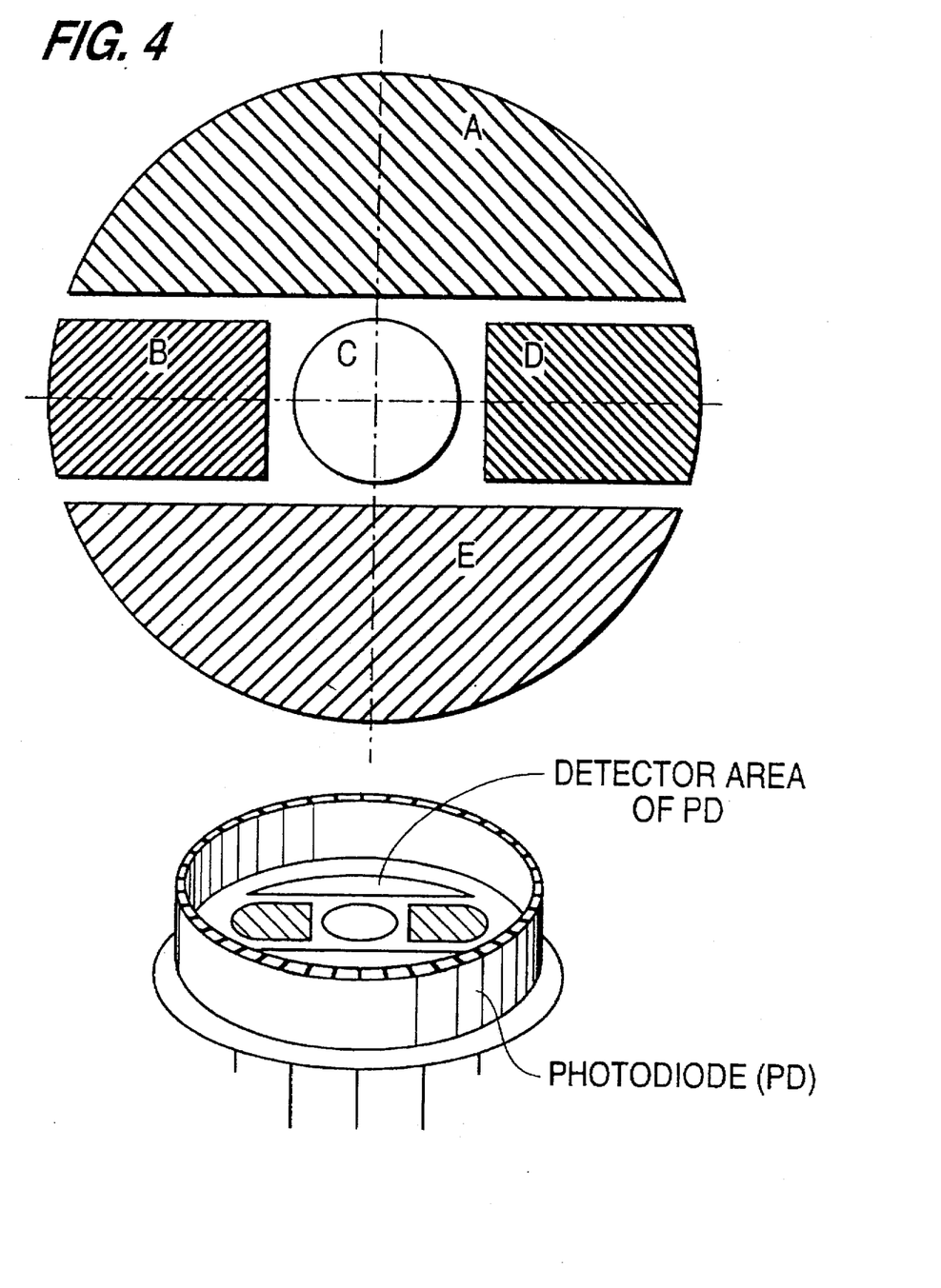
FIG. 4 illustrates, in plan and in perspective, one exemplary configuration of light-detecting surfaces of a photodiode employed in the present invention.
Figure 5:
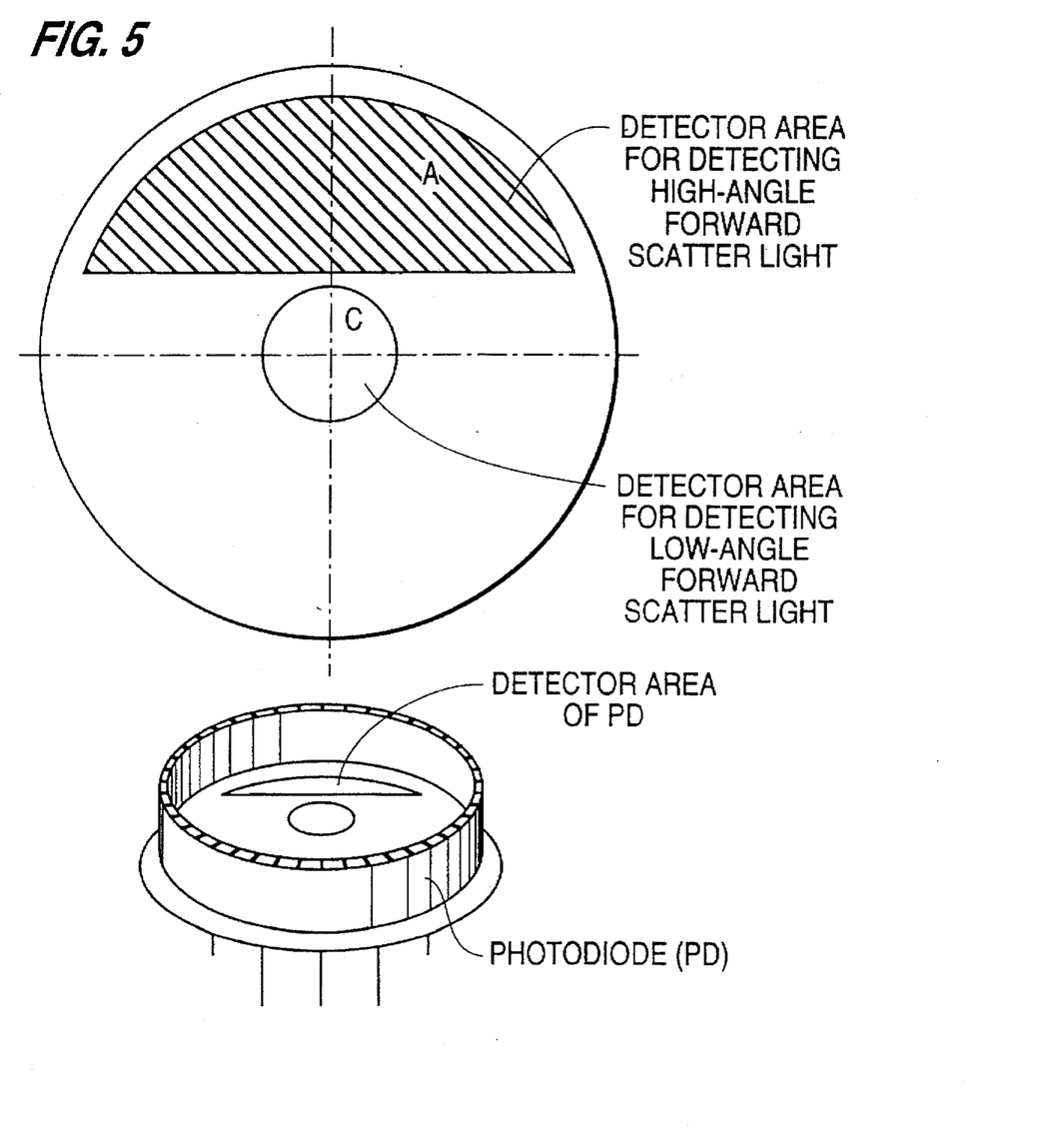
FIG. 5 illustrates, in plan and in perspective, another exemplary configuration of light-detecting surfaces of a photodiode employed in the present invention.

FIGS. 4 and 5 illustrate exemplary configurations of light-detecting surfaces of the photodiode 26.

A first exemplary photodiode shown in FIG. 4 has five separate light-detecting surfaces, i.e., a circular light-detecting surface C disposed in the center thereof, light-detecting surfaces B and D shaped as shown in FIG. 4 and disposed in a horizontally symmetrical relation with respect to the light-detecting surface C, and light-detecting surfaces A and E shaped as shown in FIG. 4 and disposed in a vertically symmetrical relation with respect to the light-detecting surface C.

A second exemplary photodiode shown in FIG. 5 has a circular light-detecting surface C disposed in the center thereof, and a semicircular light-detecting surface A disposed on the upper side of the light-detecting surface C.

As described above, the present invention utilizes two types of forward scatter light rays for cytoanalysis. In this embodiment, the photodiode 26 is adapted to detect low-angle forward scatter light rays which are scattered forward at angles between 1° and 5° with respect to the optical axis and high-angle forward scatter light rays which are scattered forward at angles between 6° and 20° with respect to the optical axis.

The low-angle forward scatter light rays reflect the size of a cell, while the high-angle forward scatter light rays reflect the inside structure of the cell. Therefore, the classification and quantification of cells are realized by analyzing signals indicative of these two types of scattered light rays.

In the photodiodes shown in FIGS. 4 and 5, the circular light-detecting surface C located in the center thereof is adapted to detect the low-angle forward scatter light rays and the other light-detecting surfaces are adapted to detect the high-angle forward scatter light rays. The light-detecting surfaces B, D and E shown in FIG. 4 are also utilized for the positional adjustment of optical system components which will be described later. It is also possible to detect the high-angle forward scatter light rays by the combination of light-detecting surfaces A, B, D and E, or the combination of opposite surfaces A and E, or B and D. The light-detecting surface C has, for example, a diameter of 1.5 mm. The light-detecting surfaces A and E are each formed into a semicircular shape having a diameter of about 6 mm, for example.

The photodiode 26 is accommodated in a metal can and has several output terminals provided on the side opposite to the light-detecting surfaces for outputting electric pulse signals indicative of the intensities of scattered light rays detected by the light-detecting surfaces. The photodiode 26 has a diameter of about 15 mm which is about one fiftieth that of a photomultiplier tube.

The output terminals are connected to a signal processor (not shown) utilizing a microcomputer. The signal processor essentially consists of an amplifier circuit, a peak detection circuit, an A/D convertor circuit and the microcomputer. The microcomputer includes a CPU, an ROM, an RAM, an I/O controller and a timer and is connected to input devices such as keyboard and mouse, a display device such as LCD or CRT and a printer, as required.

Electric pulse signals include two types of signals indicative of the intensities of the low-angle forward scatter light and high-angle forward scatter light and are output every time a cell passes through a light spotted portion of the flow cell 24.

Upon receiving such electric pulse signals, the signal processor calculates peak values, pulse widths and pulse waveform areas of the pulse signals, then derives therefrom data necessary for cytoanalysis, and classifies and counts cells.

As can be understood from the foregoing, the present invention employs a laser diode as the light source and a photodiode as the light-detecting device, thereby realizing a compact and inexpensive cytoanalyzer. For example, the size of the light source portion employing a laser diode can be reduced to less than one tenth that employing a conventional argon ion laser.

Further, the present invention employs as the light-detecting device a single photodiode having a plurality of separate light-detecting surfaces, which are adapted to separately detect two types of forward scatter light rays having relatively high intensities. Therefore, the optical system components ranging from the light source to the light-detecting device can be arranged in a line on the optical axis. Such an arrangement reduces the size of the cytoanalyzer.

Since the present invention does not utilize side scatter light which is utilized in a conventional cytoanalyzer, there is no need to provide a collector lens, pin hole, filter and light-detecting device for the measurement of the side scatter light in the cytoanalyzer of the present invention. Therefore, the size and cost of the cytoanalyzer can be reduced in comparison with the conventional cytoanalyzer. Further, the cytoanalyzer of the present invention has a reduced number of optical system components, so that the adjustment of the optical axis and other maintenance operations can be facilitated.

The present invention does not employ a light blocking device having slits to define two different angle ranges for the detection of two types of forward scatter light rays. Instead, the scatter angle ranges are defined by the shapes of separate light-detecting surfaces provided in the photodiode. This eliminates troublesome adjustment such as the positioning of the light blocking device, thereby facilitating the maintenance of the cytoanalyzer.

Next, there will be described an exemplary method for classifying leukocytes with use of the cytoanalyzer of the present invention.

A blood sample treated with a reagent is allowed to flow through the flow cell 24, and cells in a fine stream of the blood sample flowing through the flow cell 24 are subjected to a laser beam emitted from the laser diode 21.

An exemplary reagent to be preferably used for the analysis of leukocytes has the following composition:

| | |
|---|---|
| Ionic surfactant | 100–500 mg/l |
| Magnesium 8-anilino-1-naphthalenesulfonate (organic compound) | 2 g/l |
| BC30TX (nonionic surfactant available from Nikko Chemicals Co., Ltd.) | 1 g/l |
| HEPES | 10 mM |
| Methyl alcohol | 100 ml/l |

PH is adjusted to 7.0 by adding an appropriate amount of NaOH.

Herein used as the ionic surfactant is decyltrimethylammonium bromide (DTAB) in an amount of 750 ml/l, lauryltrimethylammonium chloride in an amount of 500 mg/l, myristyltrimethylammonium bromide in an amount of 500 mg/l, or cetyltrimethylammonium chloride in an amount of 100 mg/l.

Low-angle forward scatter light and high-angle forward scatter light are measured after passing 30 seconds after a mixture of 30 l of a blood sample and 1 ml of the aforesaid reagent is applied to the flow cell 24. Since only the low-angle forward scatter light and high-angle forward scatter light are detected for the cytoanalysis, there is no need to stain leukocytes with a conventionally utilized reagent for the detection of fluorescence.

More specifically, a laser beam is scattered by the leukocytes flowing through the flow cell 24, and two types of forward scatter light rays are detected by the photodiode 26.

The intensities of the scattered light rays thus detected are output to the signal processor, which in turn calculates peak values, pulse waveform areas and the like of pulse signals indicative of the light intensities.

Figure 6:
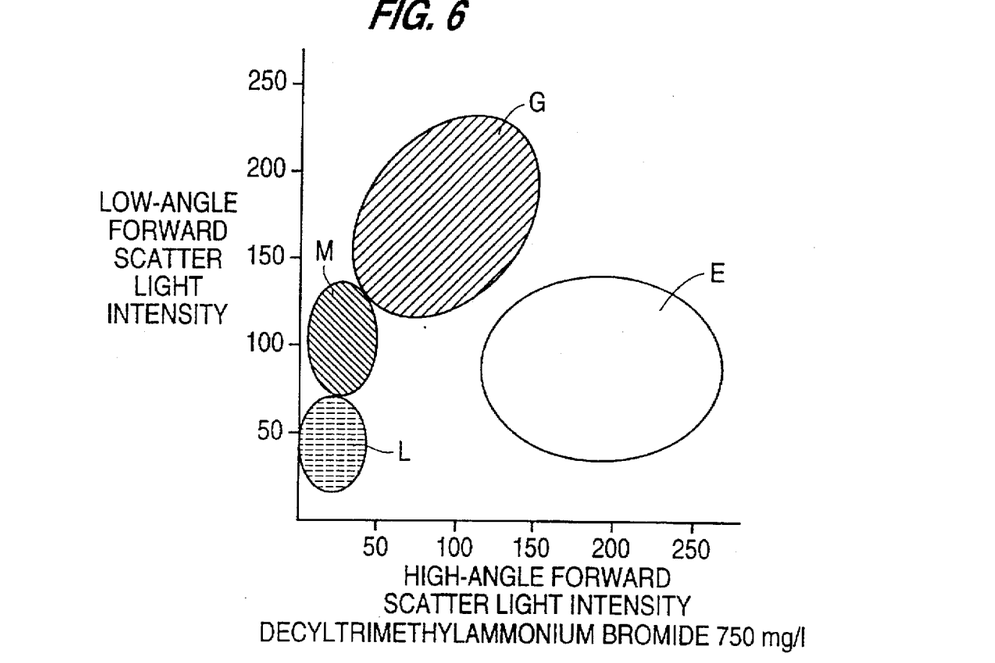
FIG. 6 is one example of a schematic scattergram obtained when leukocytes are classified by the cytoanalyzer of the present invention.
Figure 7:
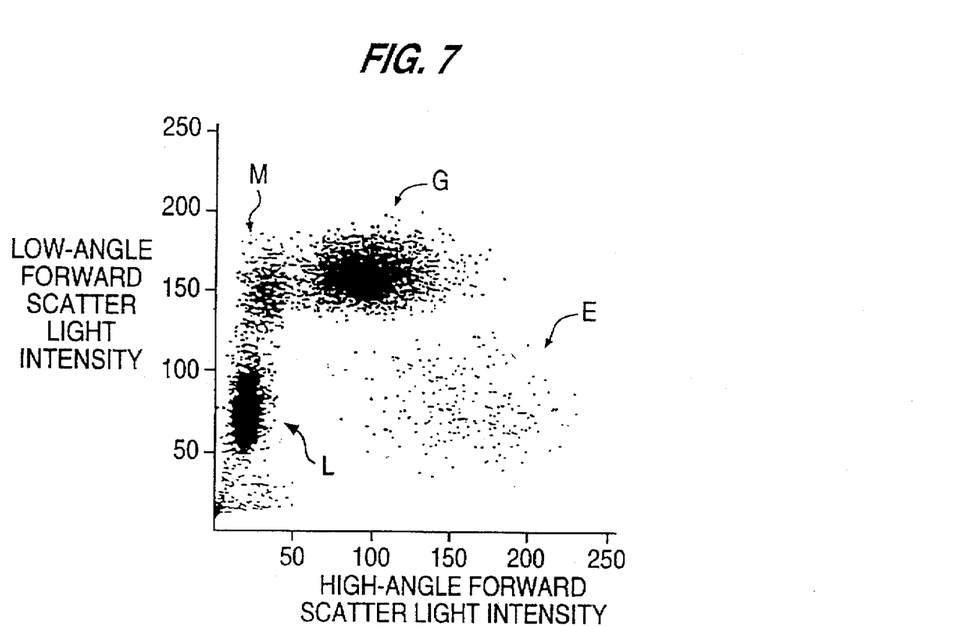
FIG. 7 is a scattergram prepared on the basis of raw data which are obtained when leukocytes are classified by the cytoanalyzer of the present invention.

Based on the values thus calculated, a scattergram is prepared as represented by the tow-angle forward scatter intensity and the high-angle forward scatter intensity. Since the relationship between the low-angle forward scatter intensity and the high-angle forward scatter light intensity varies depending on the leukocyte subclasses (or plots of the low-angle forward scatter light intensity vs. the high-angle forward scatter light intensity appear in different regions on the scattergram depending on the leukocyte subclasses), leukocytes can be classified on the basis of the scattergram. FIGS. 6 and 7 are examples of scattergrams obtained when leukocytes are classified by using the aforesaid reagent in the cytoanalyzer of the present invention. FIG. 6 is a schematic scattergram, and FIG. 7 is a scattergram prepared on the basis of raw data.

The high-angle forward scatter light intensity and the low-angle forward scatter light intensity are plotted as the abscissa and the ordinate, respectively.

As shown, leukocytes are classified into four subclasses, i.e., lymphocyte (L), monocyte (M), granulocyte (G) other than acidocyte and acidocyte (E).

Thus, the leukocytes can be classified into these four subclasses at a time by using the cytoanalyzer and the aforesaid reagent according to the present invention without the need for staining the leukocytes.

It is otherwise possible to classify the leukocytes into five subclasses by analyzing the same blood sample treated with another reagent which allows for the identification of basophil and examining these analysis results along with the aforesaid analysis results.

To be described next is a method of adjusting the optical system components of the cytoanalyzer in accordance with the present invention.

The adjustment of the optical system components is achieved by employing the photodiode having the configuration shown in FIG. 4. The optical axis and the position of the beam stopper are each adjusted by measuring output differences among light intensities detected by the five separate light-detecting surfaces of the photodiode.

FIG. 8 illustrates an exemplary method of adjusting the optical axis.

Figure 8A:
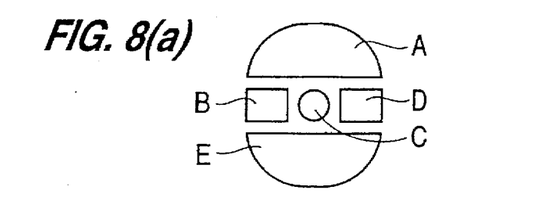
FIGS. 8a–8f are diagrams for explaining the adjustment of an optical axis in accordance with the present invention.

FIG. 8(a) is a schematic diagram illustrating the five separate light-detecting surfaces A to E of the photodiode 26 shown in FIG. 4.

Before starting the adjustment of the optical axis, the beam stopper 27 shown in FIG. 2 is removed.

Figure 8B:
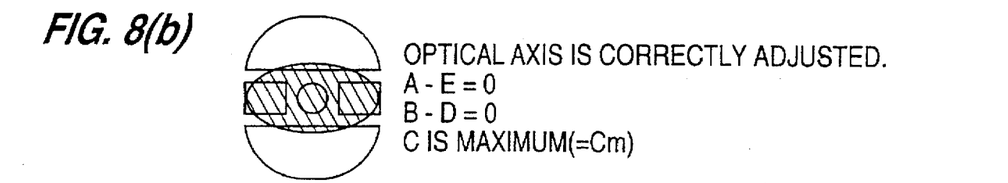

FIG. 8(b) shows a laser-beam projection when the optical axis is correctly adjusted. With the beam stopper 27 being removed, the laser beam is projected in an elliptical shape on the light-detecting surfaces on the photodiode. At this time, the laser intensities on the light-detecting surfaces B and D arranged in a horizontally symmetrical relation in the photodiode are equal to each other, and likewise the laser intensities on the light-detecting surface A and E arranged in a vertically symmetrical relation are equal to each other. The intensity of the laser beam detected by the central light-detecting surface C assumes the maximum value (Cm). If the optical axis is offset, the offset direction can be determined by measuring differences between The laser intensities on the light-detecting surfaces A and E and between those on the light-detecting surfaces B and D.

Figure 8C:
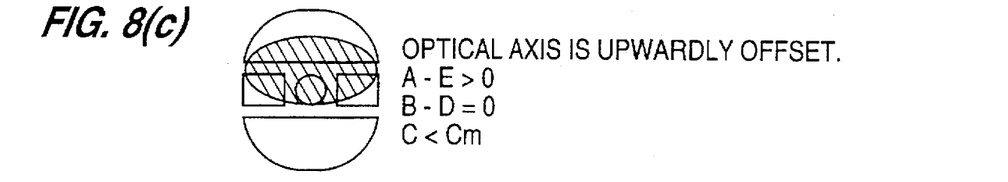

FIGS. 8(c) to 8(f) each show a laser-beam projection when the optical axis is offset.

Where the optical axis is upwardly offset as shown in FIG. 8(c), for example, the laser intensities on the light-detecting surfaces B and D are equal to each other, while the laser intensity on the light-detecting surface A is greater than that on the light-detecting surface E.

When the optical axis is to be manually adjusted, the signal processor (not shown) connected to the photodiode is allowed to measure the laser intensities and calculates values of the laser intensities on the respective light-detecting surfaces, an output difference between the laser intensities on the light-detecting surfaces A and E and an output difference between the laser intensities on the light-detecting surfaces B and D. Then, the signal processor causes the display device to display the calculation results or schematic graphics representing the offset state of the laser-beam projection as shown in FIG. 8(b) to 8(f).

While watching the display, an operator manually adjusts the position of each optical system component such as lens, for example, to downwardly move the optical axis into the state shown in FIG. 8(b).

Thus, the operator can carry out the manual adjustment of the optical axis while checking the current adjustment state displayed on the display device on a real-time basis. As seen, the optical adjustment is achieved more easily than that carried out through visual observation.

Figure 8D:
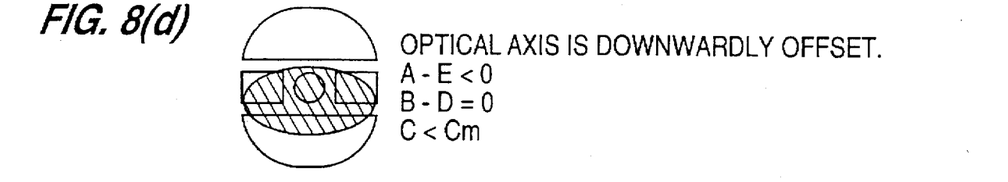
Figure 8E:
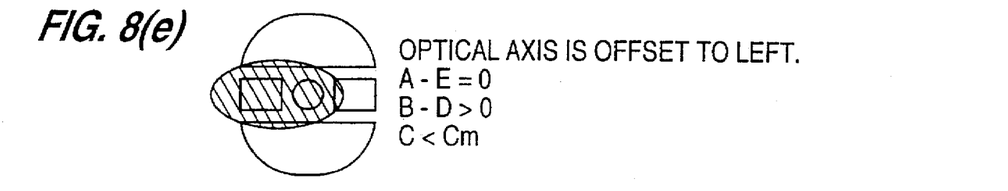
Figure 8F:
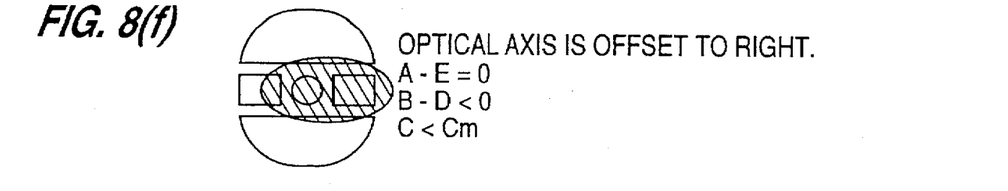

Since a more objective factor of the light intensity difference is employed as a criterion, more accurate adjustment of the optical axis can be realized. The completion of successful adjustment may preferably be notified by a sound or display color.

Where the optical axis is downwardly offset as shown in FIG. 8(d), the output difference (A–E) between the laser intensities on the light-detecting surfaces A and E is a negative value.

Where the optical axis is offset to the left as shown in FIG. 8(e), the output difference (B–D) between the laser intensities on the light-detecting surfaces B and D is a positive value.

Where the optical axis is offset to the right as shown in FIG. 8(f), the output difference (B–D) is a negative value.

In these cases, the adjustment of the optical axis is carried out in substantially the same manner as described above.

Figure 9A:
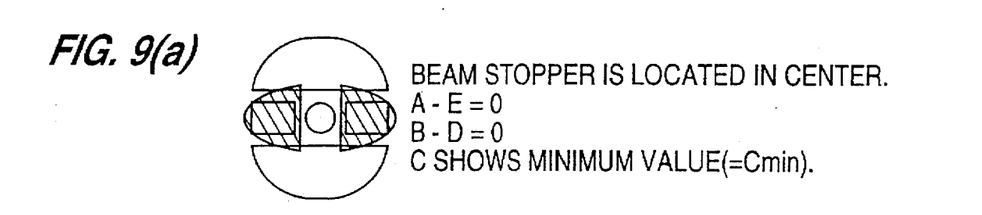
FIGS. 9a–9c for explaining the positional adjustment of a beam stopper in accordance with the present invention.
Figure 9B:
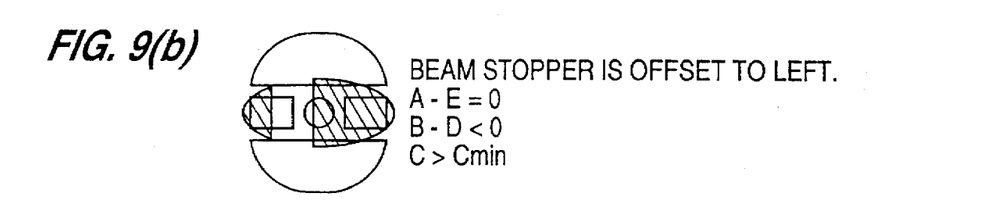
Figure 9C:
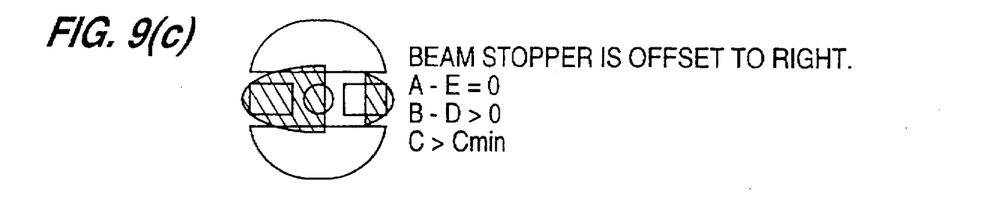

FIG. 9 illustrates an exemplary method of adjusting the position of the beam stopper.

Since the beam stopper 27 is a vertically elongated plate, a central portion of a laser beam is blocked by the beam stopper 27, and the photodiode 26 detects two separate side portions of the laser beam projected thereon as shown in FIG. 9.

Where the beam stopper 27 is correctly located in a central position as shown in FIG. 9(a), the laser intensity output differences are A–E=0 and B–D=0, and the output of the light intensity on the central portion assumes the minimum value (Cmin).

Where the beam stopper 27 is offset to the left from the central position as shown in FIG. 9(b), the laser intensity output differences are A–E=0 and B–D<0.

Where the beam stopper 27 is offset to the right from the central position as shown in FIG. 9(c), the laser intensity output differences are A–E=0 and B–D>0.

Therefore, the position of the beam stopper 27 is adjusted so that the output difference (B–D) between the laser intensities on the light-detecting surfaces B and D may assume zero. By observing the display on the display device for checking the current adjustment state, the manual adjustment of the beam stopper 27 can be easily carried out in substantially the same manner as the aforesaid adjustment of the optical axis. Since a more objective factor of the laser intensity is employed as a criterion for the positional adjustment of the beam stopper 27, like the adjustment of the optical axis, the position of the beam stopper 27 can be more accurately adjusted.

The intensity of scattered light detected by the photodiode is output as an electrical signal. Therefore, when the cytoanalyzer of the present invention further includes a mechanism for adjusting the positions of the optical system components and beam stopper and an electric driving device for actuating the position adjusting mechanism, automatic positional adjustment of the optical axis and the beam stopper can be realized.

More specifically, the optical axis and the beam stopper are automatically adjusted through a feedback control by controlling the driving device so that the laser intensity difference between appropriate light-detecting surfaces measured by the signal processor assumes zero.

As has been described, the present invention employs a semiconductor light emitting means for emitting a laser beam and a semiconductor light-detecting means having at least two photosensing portions for detecting Two types of forward scatter light rays, thereby realizing a compact and inexpensive cytoanalyzer.

The present invention utilizes pulse signals indicative of two types of forward scatter light rays scattered by leukocytes in a fine stream for the analysis of the leukocytes. Therefore, a compact and inexpensive cytoanalyzer can be realized.

Since the cytoanalyzer of the present invention is adapted to measure output differences between light intensities detected by three types of photosensing portions of the semiconductor light-detecting means and display the measurement results in a predetermined manner, the optical axis and the position of a beam stopper can be readily and accurately adjusted.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A cytoanalyzer comprising:
    a flow cell for aligning cells and permitting the same to pass therethrough;
    light emitting means for emitting a laser beam to the cells passing through the flow cell; and
    light-detecting means having at least two separate photosensing portions sensing two types of light coming from each of the cells, said light detecting means including a first photosensing portion having a single light-detecting surface, a second photosensing portion having two light-detecting surfaces disposed symmetrically with respect to a first axis with the first photosensing portion interposed therebetween, and a third photosensing portion having two-light detecting surfaces disposed symmetrically with respect to a second axis extending perpendicular to the first axis with the first photosensing portion interposed therebetween, said first axis and second axis intersecting at an optical axis of the cytoanalyzer when said light detecting means is properly centered.

2. A cytoanalyzer as set forth in claim 1 further comprising:
    first light condenser means for focusing the laser beam emitted from the semiconductor light emitting means on the flow cell;
    second light condenser means for condensing the two types of light come from the cell so as to direct the same substantially parallel to an optical axis of the laser beam emitted from the semiconductor light emitting means; and
    a beam stopper for blocking the passage of light directly emitted thereto from the semiconductor light emitting means,
    wherein the light-detecting means detects the two types of forward scatter light directed substantially parallel to the optical axis by the second light condenser means.

3. A cytoanalyzer as set forth in claim 2, further comprising:
    measurement means for measuring differences between outputs detected by the two light-detecting surfaces disposed symmetrically with respect to said first axis and photosensing portions and between outputs detected by the two light-detecting surfaces disposed symmetrically with respect to said second axis, and
    adjusting the light detecting means in accordance with said differences such that the differences are minimized.

4. A cytoanalyzer as set forth in claim 2,
    wherein the light-detecting means includes a first photosensing portion for detecting low-angle forward scatter light which are scattered forward at angles between 1° and 5° with respect to an optical axis, and a second photosensing portion for detecting high-angle forward scatter light which are scattered forward at angles between 6° and 20° with respect to the optical axis.

5. A cytoanalyzer as set forth in claim 4 further comprising:
    signal analyzing means for analyzing pulse signals indicative of the two types of forward scatter light detected by the light-detecting means,
    wherein the light-detecting means detects the two types of light scattered forward by leukocytes in a fine stream passing through the flow cell, and the signal analyzing means classifies the leukocytes.

6. A cytoanalyzer as set forth in claim 2,
    wherein the light emitting means is a light emitting device emitting a laser beam having a wavelength in a visible spectrum.

7. A cytoanalyzer set forth in claim 2 further comprising:
    measurement means for measuring differences among outputs of light detected by the photosensing portions; and
    display means for displaying measurement results obtained by the measurement means.

8. A cytoanalyzer as set forth in claim 7,
    wherein the measurement means measures a difference between outputs of light detected by the two light-detecting surfaces of the second photosensing portion and a difference between outputs of light detected by the two light-detecting surfaces of the third photosensing portion.
    wherein the display means displays the output differences.

9. A cytoanalyzer as set forth in claim 2 further comprising:
    signal analyzing means for analyzing pulse signals indicative of the two types of light detected by the light-detecting means,
    wherein the light-detecting means detects the two types of light scattered forward by leukocytes in a fine stream passing through the flow cell, and the signal analyzing means classifies the leukocytes.

10. A cytoanalyzer as set forth in claim 1,
    wherein the light-detecting means includes a first photosensing portion for detecting low-angle forward light of angles between 1° and 5° with respect to an optical axis, and a second photosensing portion for detecting high-angle forward light of angles between 6° and 20° with respect to the optical axis.

11. A cytoanalyzer as set forth in claim 10 further comprising:
    signal analyzing means for analyzing pulse signals indicative of the two types of tight detected by the light-detecting means,
    wherein the light-detecting means detects the two types of forward light come from leukocytes in a fine stream passing through the flow cell, and the signal analyzing means classifies the leukocytes.

12. A cytoanalyzer as set forth in claim 1,
    wherein the light emitting means is a light emitting device emitting a laser beam having a wavelength in a visible spectrum.

13. A cytoanalyzer as set forth in claim 1 further comprising:
    signal analyzing means for analyzing pulse signals indicative of the two types of light detected by the light-detecting means,
    wherein the light-detecting means detects the two types of light come from leukocytes in a fine stream passing through the flow cell, and the signal analyzing means classifies the leukocytes.

14. A cytoanalyzer as set forth in claim 1, further comprising:
    measurement means for measuring differences between outputs detected by the two light-detecting surfaces disposed symmetrically with respect to said first axis and photosensing portions and between outputs detected by the two light-detecting surfaces disposed symmetrically with respect to said second axis, and adjusting the light-detecting means in accordance with said differences such that the differences are minimized.

15. A cytoanalyzer as set forth in claim 1, wherein said light detecting means including a first photosensing portion having a single light-detecting surface, a second photosensing portion having two light-detecting surfaces disposed symmetrically with respect to a first axis with the first photosensing portion interposed therebetween, and a third photosensing portion having two-light detecting surfaces disposed symmetrically with respect to a second axis extending perpendicular to the first axis with the first photosensing portion interposed therebetween, said first axis and second axis intersecting at an optical axis of the cytoanalyzer when said light detecting means is properly aligned.

16. A cytoanalyzer as set forth in claim 15 further comprising:

measurement means for measuring differences among outputs of light detected by the photosensing portions; and display means for displaying measurement results obtained by the measurement means.

17. A cytoanalyzer as set forth in claim 16, wherein the measurement means measures a difference between outputs of light detected by the two light-detecting surfaces of the second photosensing portion and a difference between outputs of light detected by the two light-detecting surfaces of the third photosensing portion, wherein the display means displays the output differences.

18. A method for correctly adjusting a position of a light detector in a cytoanalyzer comprising the steps of:

providing a light detector including a first photosensing portion having a single light detecting surface, a second photosensing portion having two light-detecting surfaces disposed symmetrically with respect to a first axis with the first photosensing portion interposed therebetween, and a third photosensing portion having two-light detecting surfaces disposed symmetrically with respect to a second axis extending perpendicular to the first axis with the first photosensing portion interposed therebetween, said first axis and second axis intersecting at an optical axis of the cytoanalyzer;

providing illumination to said light-detector along said optical axis;

measuring differences between outputs detected by the two light-detecting surfaces disposed symmetrically with respect to said first axis and photosensing portions and between outputs detected by the two light-detecting surfaces disposed symmetrically with respect to said second axis; and adjusting the position the light-detector in accordance with said differences such that the differences are minimized, thereby correctly adjusting the position of the light detector.

19. The method as recited in claim 18, wherein said adjusting step includes moving said light detector along said second axis when a difference between outputs detected by the two light-detecting surfaces disposed symmetrically with respect to said first axis is not zero and moving said light detector along said first axis when a difference between outputs detected by the two light-detecting surfaces disposed symmetrically with respect to said second axis is not zero.

* * * * *